(12) United States Patent
Fujisaki et al.

(10) Patent No.: US 7,824,376 B2
(45) Date of Patent: Nov. 2, 2010

(54) INJECTION NEEDLE APPARATUS FOR MAKING INJECTION IN TISSUE IN BODY CAVITY

(75) Inventors: Ken Fujisaki, Hachioji (JP); Kiyotaka Matsuno, Sagamihara (JP)

(73) Assignee: Olympus Corporation (JP)

( * ) Notice: Subject to any disclaimer, the term of this patent is extended or adjusted under 35 U.S.C. 154(b) by 261 days.

(21) Appl. No.: 11/722,303

(22) PCT Filed: Dec. 20, 2005

(86) PCT No.: PCT/JP2005/023409
§ 371 (c)(1),
(2), (4) Date: Mar. 12, 2008

(87) PCT Pub. No.: WO2006/068154
PCT Pub. Date: Jun. 29, 2006

(65) Prior Publication Data
US 2009/0043258 A1    Feb. 12, 2009

(30) Foreign Application Priority Data
Dec. 24, 2004  (JP)  .............................. 2004-374991
Dec. 24, 2004  (JP)  .............................. 2004-374992

(51) Int. Cl.
A61M 5/178  (2006.01)

(52) U.S. Cl. .................. 604/164.01; 604/264; 604/272; 600/106

(58) Field of Classification Search ............ 604/164.01, 604/165.01, 188, 273, 274, 264, 272; 600/106, 600/567
See application file for complete search history.

(56) References Cited

U.S. PATENT DOCUMENTS

| | | | | |
|---|---|---|---|---|
| 3,856,253 A | * | 12/1974 | Seebinger | .................. 248/411 |
| 5,346,480 A | * | 9/1994 | Hess et al. | .................. 604/197 |
| 5,353,804 A | | 10/1994 | Kornberg et al. | ............ 128/754 |
| 5,766,184 A | | 6/1998 | Matsuno et al. | ............. 606/142 |
| 2001/0005778 A1 | | 6/2001 | Ouchi | ........................ 600/564 |

(Continued)

FOREIGN PATENT DOCUMENTS
JP    2001 058006    3/2001

(Continued)

OTHER PUBLICATIONS

Extended Search Report by the European Patent Office for European Patent Application No. 05819987.8-2320 issued Mar. 2, 2009.

(Continued)

*Primary Examiner*—Nicholas D Lucchesi
*Assistant Examiner*—Jenner Yeh
(74) *Attorney, Agent, or Firm*—Ostrolenk Faber LLP

(57) ABSTRACT

An injection needle apparatus in which an operation for relatively moving an outer tube 4 and an inner tube 5 is performed to project and retract a needle body 12 from and into a distal end of the outer tube 4, and to carry out a movement of rotation of the needle body 12 at a predetermined angle by relative forward and backward movements of the outer tube 4 and inner tube 5 in their longitudinal directions every time the forward and backward movement operations is repeated, thereby enabling changing a direction of a needlepoint 14 of the needle body 12 at each angle.

21 Claims, 6 Drawing Sheets

U.S. PATENT DOCUMENTS

2002/0095168 A1 7/2002 Griego et al. ............... 606/167
2004/0111064 A1* 6/2004 Asbaghi .................... 604/198

FOREIGN PATENT DOCUMENTS

| JP | 2003 144436 | 5/2003 | |
| WO | WO 93/16644 | 9/1993 | |
| WO | WO 2004/004565 | * | 1/2004 |
| WO | WO 2006/058328 | | 6/2006 |

OTHER PUBLICATIONS

International Search Report PCT/JP2005/023409 dated Apr. 3, 2006.
International Preliminary Report on Patentability in corresponding PCT Appln. No. PCT/JP2005/023409 dated Jul. 5, 2007.

* cited by examiner

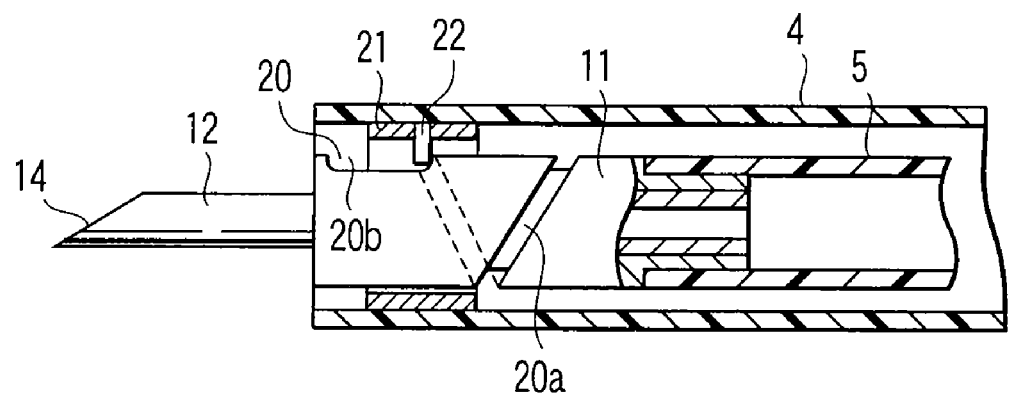
F I G. 9
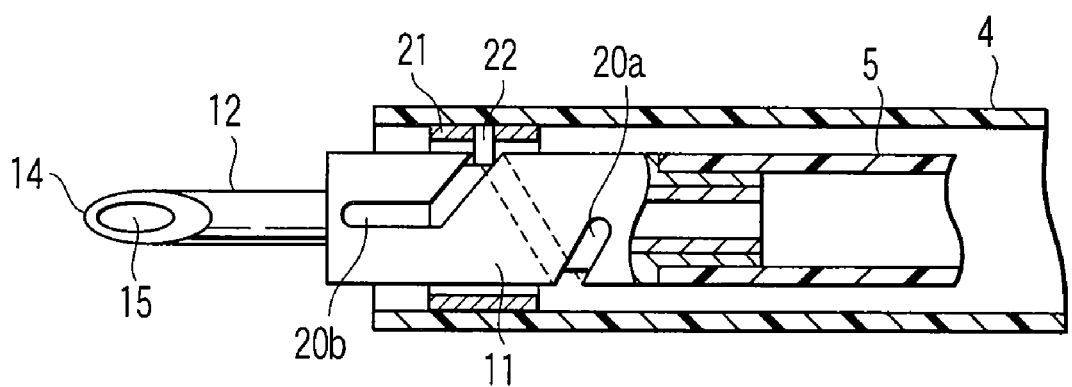
F I G. 10

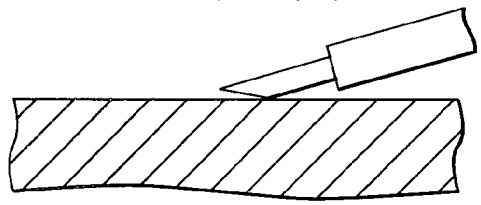
FIG. 11A (Needlepoint pointing upward)
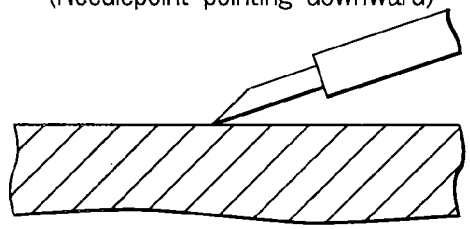
FIG. 11B (Needlepoint pointing downward)
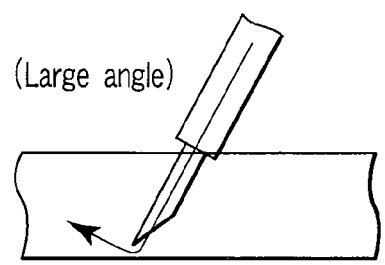
FIG. 12A (Large angle)
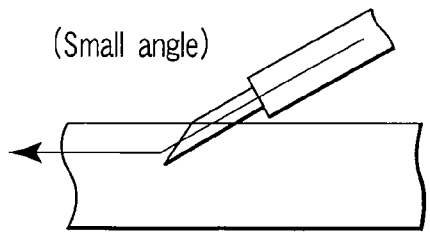
FIG. 12B (Small angle)

INJECTION NEEDLE APPARATUS FOR MAKING INJECTION IN TISSUE IN BODY CAVITY

CROSS REFERENCE TO RELATED APPLICATION

The present application is a 35 U.S.C. §§371 national phase conversion of PCT/JP2005/023409, filed Dec. 20, 2005, which claims priority of Japanese Patent Application No. 2004-374991, filed Dec. 24, 2004 and Japanese Patent Application No. 2004-374992, filed Dec. 24, 2004 the disclosure of which are herein incorporated by reference. The PCT International Application was published in the Japanese language.

TECHNICAL FIELD

This invention relates to an injection needle apparatus that is preferably used with an endoscope and injects a liquid medicine, etc. into a tissue or a tissue region such as a blood vessel in a cavity of a living body.

BACKGROUND ART

It has been done that an injection needle is introduced into a body cavity through an instrument, such as a channel, of an endoscope and a liquid medicine is injected into a tissue region, such as an organ or a blood vessel, in a body cavity by the injection needle. This type of injection needle has a double sheath structure in which an inner tube having a distal end provided with an injection needle body is inserted in an outer sheath, as disclosed in JP-A 2001-58006 (KOKAI).

When using this type of injection needle, the following procedure is carried out. First, a syringe filled with a liquid medicine is attached to a mouthpiece on a proximal end of the inner tube. Then, the outer sheath in this state is inserted into the channel of the endoscope to make the distal end of the outer sheath project from the distal end of the endoscope. Then, the inner tube is pushed inward to project out the injection needle body from the distal end of the outer sheath and to insert the injection needle body into the tissue region. Finally, the syringe is pushed to inject the liquid medicine into the tissue region.

DISCLOSURE OF INVENTION

As disclosed in the above described Patent Document 1, since a needlepoint of the conventional injection needle for an endoscope is formed by obliquely cutting the distal end part of the hollow needle body, the needlepoint has a shape that is located in one side thereof. Therefore, a position of the needlepoint and a state of the obliquely cut surface vary depending on a rotation position of the needle body, and hence a use condition also changes.

That is, as shown in FIG. 11A, when a needle is to be inserted into a tissue region such as a blood vessel in a state where the needlepoint points upward, the oblique base portion of the needlepoint is apt to come into contact with an outer surface of the tissue. Further, the oblique base portion slides on the outer surface of the tissue region and the sharp needlepoint readily moves away from the tissue region, and hence the needlepoint is hard to insert into the tissue region.

However, as shown in FIG. 11B, when the needle is to be inserted into the tissue region where the needlepoint points downward, the sharp needlepoint moves closer to the tissue region so that the needlepoint is apt to be caught on the outer surface of the tissue region and hence the needlepoint is easy to insert into the tissue region.

Moreover, as shown in FIG. 11A, when the needle is to be inserted into the blood vessel in the state where the needlepoint points upward, the oblique base portion of the needlepoint comes into contact with the blood vessel and the blood vessel moves away, thereby making it difficult to catch the blood vessel. As shown in FIG. 12A, when an angle between a tissue surface of the blood vessel and an axial direction of the needle is increased, the needlepoint easily catch the blood vessel. Therefore, the angle must be increased to make the insertion being easy. However, as shown in FIG. 12A, when the angle between the blood vessel and the axial direction of the needle is increased to make the insertion, a region where the needlepoint and the blood vessel are crossed becomes narrow to make it hard to catch the blood vessel, and to cause a problem that the needle body readily pierces the blood vessel after the needle body is inserted into the blood vessel.

Additionally, as shown in FIG. 11A, when the tip end of the needle body points upward, the distal end opening of the needle faces downward. And, the opening of the needlepoint is closed by the blood vessel wall when making the insertion in this direction, thereby degrading an injection and supply of the liquid medicine.

On the other hand, as shown in FIG. 11B, when making the insertion while the needlepoint points downward, the needlepoint can be surely inserted without slipping on the tissue surface even though the angle between the tissue surface and the needle is small, and the needle body can readily catch the blood vessel and can be readily inserted into it. Further, a pain of a patient can be relieved. Furthermore, when making the insertion into the blood vessel while the needlepoint points downward, as shown in FIG. 12B, the injection needle is arranged in the blood vessel in substantially parallel to the longitudinal direction of the blood vessel. Therefore, it is advantageous that flow paths of both the blood vessel and the needle become close to a straight line, thereby improving the injection and supply of the liquid medicine.

As explained above, it has been desirable that inserting the injection needle for an endoscope in a posture where its needlepoint points downward with respect to a tissue region in a body cavity.

However, since the injection needle for an endoscope is introduced into the body cavity through a channel of an instrument such as an endoscope, a pointing direction of the needlepoint of the injection needle when the injection needle is introduced into the body cavity is relatively determined in accordance with an introduction state of the injection needle itself, an introduction state of the instrument such as the endoscope, or a state of the tissue in the body cavity, and it cannot be specified at a time when the introducing operation is performed.

Thus, in order to select the direction of the needlepoint of the injection needle, an operation for determining the direction of the needlepoint of the injection needle is required after the injection needle is introduced into the body cavity.

However, in the conventional injection needle for an endoscope, an operation for accurately determining the direction of the needlepoint is very difficult for the following reasons. For example, since the injection needle is attached to the distal end of the inner tube inserted into the outer sheath, the inner tube may relatively rotate with respect to the outer sheath when the injection needle is inserted into the channel of the endoscope to be guided to a desired position, thereby changing a positional relationship between the outer sheath and the direction of the needlepoint of the injection needle. Even if the inner tube is rotated at an operator's side to change the direction of the needlepoint of the injection needle, the inner tube is twisted in the outer sheath so that an amount of an operating force or an amount of rotation thereof is absorbed or decreased while it is transmitted through the long inner tube, and it is not accurately transmitted to the needlepoint of the injection needle at the distal end.

Moreover, an mount of a twisting force when the inner tube is twisted is not directly transmitted to the distal end of the inner tube due to a friction force between the outer sheath and the inner tube, and an unexpected rotation of the injection needle may be caused. In a case that the twisting force generated by the twisting operation is stored in the inner tube and a storage of the twisting force reaches a limit of a friction holding force, it is released at one time and the inner tube and the injection needle may rotate overly. Because of these situations, it is difficult to determine the direction of the needlepoint of the injection needle in the body cavity.

It is an object of the present invention to provide an injection needle for an endoscope, which can select a direction of a needlepoint in a body cavity, in that direction the needle body being able to be surely inserted into a tissue in the body cavity, thereby reducing a burden of an operator and a pain of an patient.

One embodiment according to this invention is an injection needle apparatus for making injection in a tissue in a body cavity, comprises:

an elongated outer tubular member that is inserted into a body cavity and has a central axis in a longitudinal direction;

an elongated inner tubular member that is inserted into the outer tubular member, movable in the longitudinal central axis direction of the outer tubular member, and has a central axis in a longitudinal direction;

a needle body for insertion that is supported at a distal end part of the inner tubular member and has a distal end sharp part eccentrically arranged from the longitudinal central axis to a lateral side of the inner tubular member;

an operating portion that is placed on a proximal end side of the inner tubular member, operates a proximal end part of the inner tubular member to move the inner tubular member in the longitudinal axis direction of the outer tubular member, and projects and retracts the needle body from and into a distal end of the outer tubular member; and a needle body rotation operating device that is provided at the distal end part of the inner tubular member, and rotates the needle body around the central axis in the longitudinal axis direction of the inner tubular member by the movement of the inner tubular member in the longitudinal axis direction to change a position of the distal end sharp part.

BRIEF DESCRIPTION OF DRAWINGS

FIG. 9 is a vertical cross-sectional view of a distal end part of the injection needle apparatus for an endoscope, according to the other embodiment of the present invention, in a state where a needle body is projected;

FIG. 10 is a vertical cross-sectional view of the distal end part of the injection needle apparatus for an endoscope, according to the other embodiment of the present invention, in a state where the needle body is rotated;

FIG. 11A is a view for explaining an inserting state of an injection needle apparatus for an endoscope into a tissue in a body cavity;

FIG. 11B is a view for explaining an inserting state of the injection needle apparatus for an endoscope into the tissue in the body cavity;

FIG. 12A is a view for explaining an inserting state of the injection needle apparatus for an endoscope into a blood vessel in a body cavity; and FIG. 12B is a view for explaining an inserting state of the injection needle apparatus for an endoscope into the blood vessel in the body cavity.

BEST MODE FOR CARRYING OUT THE INVENTION

Embodiments of the present invention will now be explained hereinafter with reference to the accompanying drawings.

Figure 1:
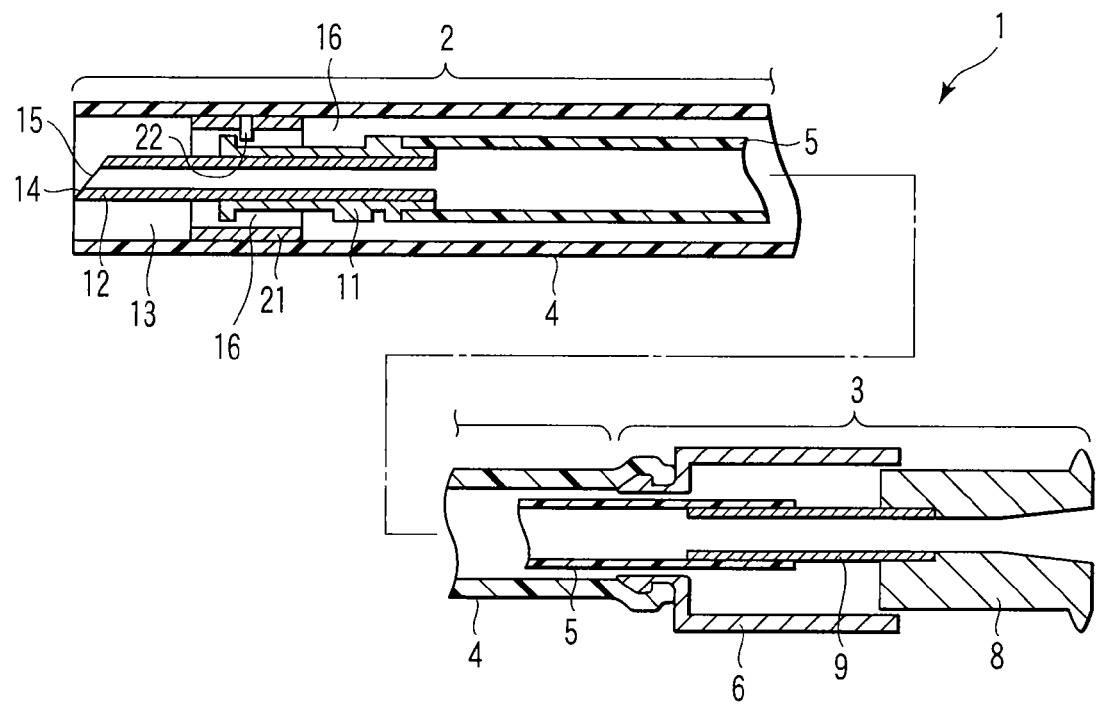
FIG. 1 is a vertical cross-sectional view of an injection needle apparatus for an endoscope, according to one embodiment of the present invention.

FIGS. 1 to 8 show an injection needle apparatus for an endoscope, according to one embodiment of the present invention. As shown in FIG. 1, an injection needle apparatus 1 for an endoscope is configured to be divided into an inserting portion 2 and an operating portion 3. The inserting portion 2 has a flexible outer tube (an outer sheath) 4 as an outer tube member and a flexible inner tube 5 configuring a part of an inner tube member, and the inner tube 5 is inserted into the outer tube 4 to be movable back and forth along a longitudinal axis direction of the inner tube 5. Both the outer tube 4 and the inner tube 5 have a relationship that they can relatively move in a central axis direction in a longitudinal direction of the inserting portion 2. The outer tube 4 and the inner tube 5 are formed of a resin having elasticity, e.g., fluoroplastic, polyethylene, polyamide, and the like.

As shown in FIG. 1, the operating portion 3 is configured to include an operating portion main body 6 and a mouth piece 8 serving as a slide operation member that is freely movable in a back-and-forth direction with respect to the operating portion main body 6. The mouth piece 8 is an operation member of the operating portion that operates a proximal end part of the inner tube 5 to move the inner tube 5 in the longitudinal axis direction of the outer tube 4 so that a needle body 12 explained later is projected from and retracted into the distal end of the outer tube 4.

A proximal end of the outer tube 4 is attached and fixed to the operating portion main body 6 by fixing means, e.g., press fitting, an adhesive, and the like. The mouth piece 8 is fixedly connected to the proximal end part of the inner tube 5 through a hard pipe 9 by, e.g., press fitting, an adhesive, and the like. The mouth piece 8 communicates with the inner tube 5 via the hard pipe 9. A non-illustrated syringe for injecting a liquid medicine can be detachably attached to the mouth piece 8.

As shown in FIG. 1, a cylindrical hard adapter 11 is fixedly supported at the distal end of the inner tube 5 by fixing means, e.g., an adhesive, caulking, and the like. The adapter 11 and the inner tube 5 configure the inner tube member. A hollow needle body 12 for insertion is fitted in the adapter 11, and the adapter 11 and the hollow needle body 12 are fixed by fixing means, e.g., an adhesive, caulking, and the like in a state where a distal end part of the needle body 12 projects from a distal end of the adapter 11 to be exposed. The adapter 11 and the needle body 12 are coaxially arranged with respect to a longitudinal central axis of the inner tube 5. A distal end part for insertion of the needle body 12 projected from the distal end of the adapter 11 is narrower than a diameter of the adapter 11, and a distal end of the exposed part projecting from the distal end of this adapter 11 constitutes a tissue insertion portion 13 (see FIG. 2). The adapter 11 and the needle body 12 are coaxially arranged, and both of them constitute a distal end needle portion. Here, the adapter 11 constitutes a distal end part of the inner tube, and a part of a rotation mechanism for rotating the needle body 12 is incorporated in this part.

Figure 2:
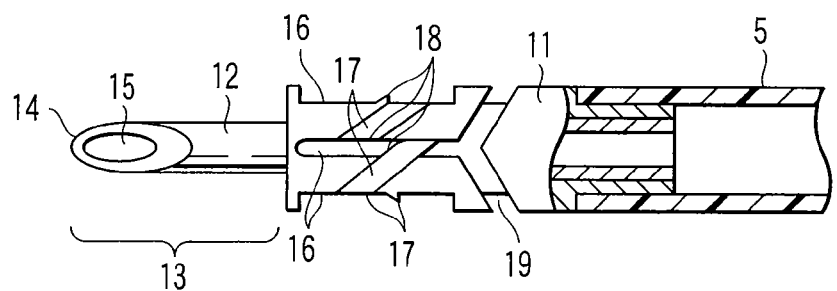
FIG. 2 is a plan view showing a distal end needle portion of the injection needle apparatus for an endoscope, a part of the needle portion being cut.

As shown in FIGS. 1 and 2, the adapter 11 projects from the distal end of the inner tube 5, and the distal end part of the needle body 12 further projects from the distal end of this adapter 11. An endmost part of the needle body 12 is obliquely cut so that a needlepoint 14 as a distal end sharp portion having a sharp shape that is eccentric with respect to the longitudinal central axis of the inner tube 5 and a distal end opening portion 15 are formed in the distal end of the needle body 12. As shown in FIGS. 1 and 2, an exposed outer peripheral part of the adapter 11 projecting from the distal end of the inner tube 5 is formed to have an external diameter substantially equal to an external diameter of the inner tube 5.

Figure 3A:
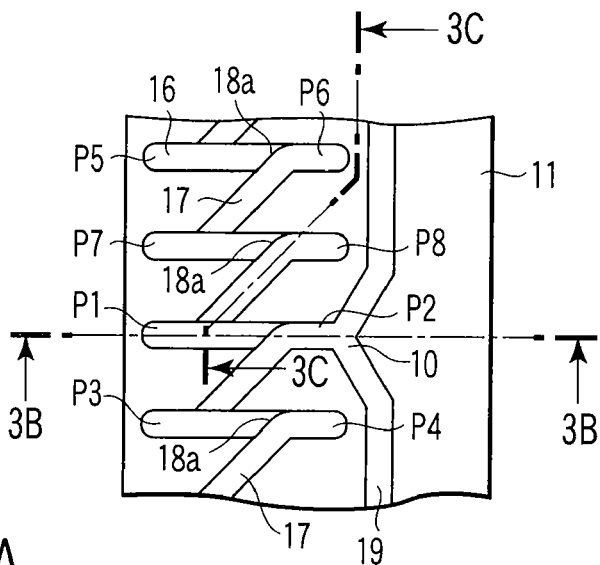
FIG. 3A is a development view of a plurality of types of groove portions formed in an adapter of the injection needle apparatus for an endoscope.

A plurality of types of grooves that engage with a projection 22 for a rotation mechanism explained later is engraved in the exposed outer peripheral surface of this adapter 11. FIG. 3A shows the part of the grooves in a developing manner. Grooves of a first type are regulating grooves for regulating a needle direction, and they are a plurality of linear grooves 16 for regulation which are formed in the circumferential outer peripheral surface of the adapter 11 to be apart from each other in the circumferential direction at each fixed angle and respectively extend in the longitudinal axial direction of the inserting portion 2. In this embodiment, the four linear grooves 16 are provided to be apart from each other at equal intervals of 90°. Of course, they will not be restricted to this state, and they may be separated from each other at intervals of more than 90° or less than 90°. When these grooves are arranged at intervals of less than 90°, the adapter 11 with the needle body 12 can be finely rotated around the central axis of the needle body 12 as can be understood from an operation explained later. The intervals at which the linear grooves 16 are arranged may not be equal intervals, and the grooves may be apart from each other at each any arbitrary angle.

Grooves of a second type are spiral grooves 17 for communication that respectively connect the linear grooves 16 adjacent to each other. Each of these spiral grooves 17 is a spirally inclined groove to connect a proximal end part of one linear groove 16 with a distal end part of a neighboring linear groove 16.

A groove of a third type is a loop-like groove 19 that is connected with the proximal end of at least one of the plurality of linear grooves 16 for fixing needle direction, placed on the proximal end side apart from this linear groove 16, and formed circularly and continuously in the entire circumference of the exposed outer peripheral surface of the adapter 11. The loop-like groove 19 is a circumferential groove that is continuous with the proximal end of the one linear groove 16 serving as a reference, arranged on the circumferential outer peripheral surface of the adapter 11, and makes a one circle on the exposed outer peripheral surface of the adapter 11. This circumferential groove constitutes torsion releasing means that leads the projection 22 explained later to the loop-like groove 19 when the inner tube 5 is twisted, thereby releasing the twist of the inner tube 5. As shown in FIG. 3A, a part of this loop-like groove 19, especially a connection part being continuous with the proximal end of the linear groove 16, has an inclination that is more modest than the spiral groove 17, and the other part is formed in a direction orthogonal to the longitudinal axis direction of the inserting portion 2.

A width of each of the grooves 16, 17, and 19 is approximately 0.5 mm which can guide the later-explained projection 22, and a depth of each of these grooves is approximately 0.3 mm in accordance with the projection 22.

One of guiding means that regulates the movement of the later-explained projection 22 by the relative back-and-forth movements of the outer tube 4 and inner tube 5 in the longitudinal direction, is provided at a position of a junction of the linear groove 16 and spiral groove 17. For example, a guide portion configured by, e.g., an angled protruding portion that protrudes from the bottom surface of the groove or a step between the bottom surfaces of the grooves is formed to provide guide means for course switching that prevents a reverse movement of the projection 22 and regulates the movement of the same. More specifically, the guide means is configured as follows.

Figure 3B:
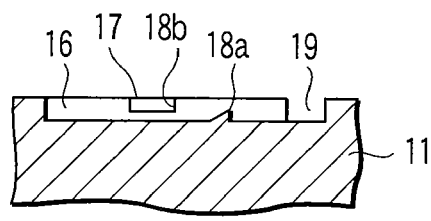
FIG. 3B is a cross-sectional view taken along a line 3B-3B in FIG. 3A.
Figure 3C:
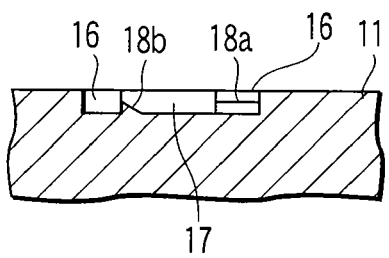
FIG. 3C is a cross-sectional view taken along a line 3C-3C in FIG. 3A.

That is, as shown in FIGS. 3A to C, at the junction of the one linear groove 16 and spiral groove 17, a step portion over which the projection 22 can move from this linear groove 16 to the spiral groove 17 communicating with the neighboring next linear groove 16 is formed as a mountain-like portion 18*a* protruding from the groove bottom surface. A part of the angled portion 18*a* located in a side of the proximal end of the one linear groove 16 is formed as a steep step, and a part of the angled portion 18*a* located in a side of the distal end of the same one linear groove 16 is formed as a moderate inclined surface. Therefore, the projection 22 placed at the distal end side groove portion of the one linear groove 16 can readily move over the angled portion 18*a* to the proximal end side portion of the linear groove 16, but is prevented from making a reverse movement as a movement toward the distal end side portion of the linear groove 16 and is caused to be guided to a movement to the region of the spiral groove 17 communicating with the neighboring linear groove 16. If the projection 22 is placed at the proximal end side portion of the linear groove 16, the projection 22 cannot move to the distal end side portion of the linear groove 16 by the angled portion 18*a*, and is regulated to be guided to the spiral groove 17 communicating with the adjacent linear groove 16.

Moreover, at a junction of a guided distal end of the spiral groove 17 toward which the projection 22 is guided and neighboring linear groove 16, an angled portion 18*b* protruding from the bottom surface of the groove is formed. A part of the angled portion 18*b* located in a side of the neighboring linear groove 16 is formed as a steep step, and a part of the angled portion 18*a* located from the side of the spiral groove 17 to the side of the neighboring linear groove 16 is formed as a moderate inclined surface. Therefore, the projection 22 can move from the spiral groove 17 to the neighboring linear groove 16, but the projection 22 that has entered in the neighboring linear groove 16 comes into contact with the step of the angled portion 18b and cannot return to the region of the original spiral groove 17.

After the projection 22 placed at the distal end side groove part of the one linear groove 16 moves to the proximal end side groove part of this linear groove 16, it cannot return to the region of the distal end side groove portion of the same linear groove 16 and moves to a region of the distal end side groove portion of the neighboring linear groove 16 through the spiral groove 17. Each angled portion 18a or 18b constitutes guiding means that regulates the movement of the projection 22. In this embodiment, the guiding means is the angled portions 18a, 18b on the bottom surfaces of the grooves near the junctions, but guide portions that prevent the reverse movement of the projection 22 and regulates the movement of the same may be configured by steps formed by height differences between the bottom surfaces of the grooves.

Figure 4:
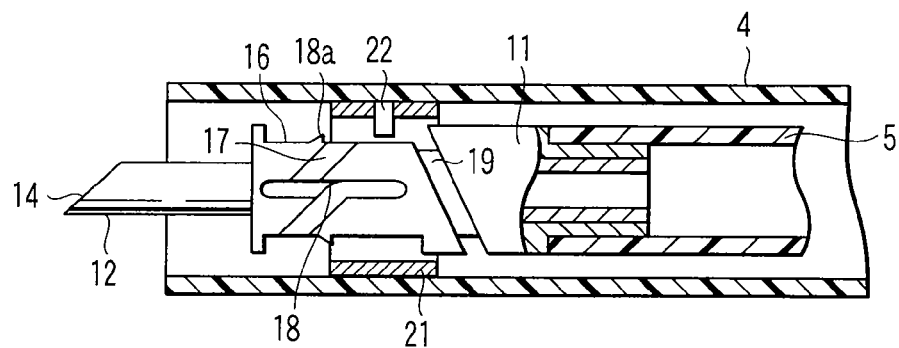
FIG. 4 is a vertical cross-sectional view of a distal end part of the injection needle apparatus for an endoscope, in a state where a needle body is projected.

As shown in FIG. 4, a pipe-like member 21 formed of a resin or a metal material is arranged on an inner surface of the distal end part of the outer tube 4 corresponding to the adapter 11, and it is fixed to the outer tube 4 by fixing means, e.g., an adhesive, press fitting, and the like. The cylindrical or semispherical projection 22 is formed on an inner surface of this pipe-like member 21 to project toward the inner side of the outer tube 4. The projecting end part of this projection 22 is always set in and engaged with the groove 16, 17, or 19, thereby regulating the movement thereof. Dimensions of the projecting part of this projection 22 is approximately 0.4 mm in its diameter and approximately 0.2 mm in its projecting height, and these dimensions are set to allow the movement of the projection 22 in the groove 16 without coming off the groove 16.

Now, an operation of the injection needle for an endoscope according to the embodiment of the present invention will be explained. When using the injection needle apparatus 1 for an endoscope, at first the mouth piece 8 is pulled toward an operator's side in the operating portion 3 with respect to the operating portion main body 6 to retract and accommodate the needle body 12 in the outer tube 4, thereby providing a preparation state as shown in FIG. 1. In this needle body accommodated state, the projection 22 is placed at the distal end side part of the linear groove 16 (a position of P1 shown in FIG. 3A).

Then, a syringe (not shown) filled with a liquid medicine is attached to the mouth piece 8 of the injection needle apparatus 1 for an endoscope.

Further, the inserting portion 2 of the injection needle apparatus 1 for an endoscope is inserted into a channel of an endoscope or any other guide instrument to be led into a body cavity so that the distal end of the inserting portion 2 is projected into the body cavity.

Then, the mouth piece 8 is pushed toward the distal end side while holding the operating portion main body 6. The projection 22 moves to the proximal end side part in the linear groove 16, and the projection 22 gets on the inclined surface of the angled portion 18a as shown in FIG. 4 and moves over the angled portion 18a to the proximal end side region of the linear groove 16 (a position of P2 shown in FIG. 3A). At this time, as shown in FIG. 4, the needle body 12 projects from the distal end of the outer tube 4 so that it is set in a state at which the needle body 12 can be inserted into a living tissue. At this time, a position of the needle body 12 around the central axis is determined in accordance with a position of the linear groove 16 at which the projection 22 is placed.

Figure 5:
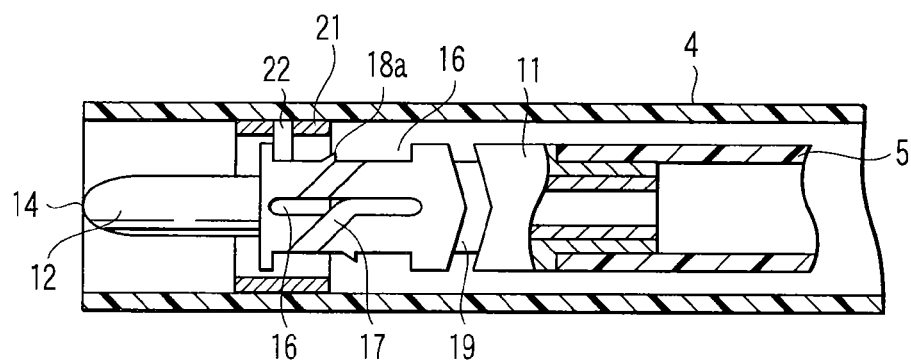
FIG. 5 is a vertical cross-sectional view of the distal end part of the injection needle apparatus for an endoscope, in a state where the needle body is retracted.

In this state where the needle body 12 projects, the direction of the needlepoint 14 of the needle body 12 around the central axis is confirmed by, e.g., the endoscope, and the like. And, when the direction of the needlepoint 14 does not point a predetermined tissue side, an operation for pulling the mouth piece 18 with respect to the operating portion main body 6 is performed once. By performing the operation for pulling the mouth piece 18, the projection 22 moves forward in the linear groove 16, but it comes into contact with the step of the angled portion 18a, and hence it cannot return to the distal end side part of the same linear groove 16. However, the projection 22 is guided by the step of the angled portion 18a to the spiral groove 17 for communication that is continuous with this linear groove 16, and it moves to the spiral groove 17. Furthermore, the projection 22 gets on the inclined surface of the angled portion 18b at the junction of the neighboring linear groove 16, and moves over the angled portion 18b and enters in a region of the distal end side part of the neighboring linear groove 16 as shown in FIG. 5. Finally, the projection 22 is placed in the distal end region of the neighboring linear groove 16 to which the projection 22 has been moved (a position of P3 shown in FIG. 3A). At this time, the needle body 12 is retracted in the outer tube 4.

Figure 6:
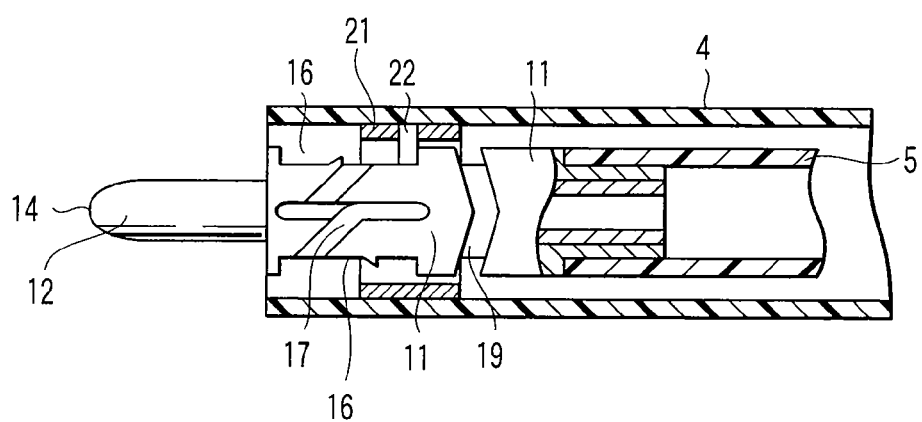
FIG. 6 is a vertical cross-sectional view of the distal end part of the injection needle apparatus for an endoscope, in a state where the needle body is rotated.

Then, the mouth piece 8 is pushed again. By this pushing operation, the projection 22 moves over the angled portion 18a of the linear groove 16 as described above and linearly moves into the region of the proximal end side portion of the same linear groove 16 (a position of P4 shown in FIG. 3A). As shown in FIG. 6, the needle body 12 takes again in the state where it projects from the outer tube 4. However, the direction of the needlepoint 14 with respect to the outer tube 4 is changed at an angle of 90° around the axis.

As described above, by performing the operation of pulling and pushing the mouth piece 8 once, the needle body 12 can be rotated around the central axis of the needle body 12 with respect to the outer tube 4 so as to move the needlepoint 14 at each fixed angle (90° in this embodiment) between the linear grooves 16 adjacent to each other. When the needle body 12 is rotated, the outer tube 4 does not rotate because a frictional resistance of the outer tube 4 to the instrument, e.g., the endoscope and the like is large. Therefore, only the needle body 12 rotates and changes the direction of the needlepoint 14.

The operation for rotating the needle body 12 is repeated until the direction of the needlepoint 14 becomes optimum with respect to the tissue in the body cavity, thereby determining the direction of the needlepoint 14 of the needle body 12. After the needlepoint 14 of the needle body 12 points the living tissue side, the outer tube 4 led out from the proximal side of the endoscope is pushed with respect to the endoscope to insert the tissue insertion portion 13 of the needle body 12 into the living tissue.

Then, the syringe is operated to inject, e.g., the liquid medicine and the like into the living body tissue through the inside of each of the mouth piece 8, the inner tube 5, and the needle body 12, thereby performing a predetermined treatment.

In order to further change the direction of the needlepoint 14 of the needle body 12, the operation of pushing and pulling the mouth piece 8 is repeated to further rotate the needle body 12 around the central axis. The needle body 12 takes one rotation via positions P5, P6, P7, and P8 shown in FIG. 3A to return to its initial state shown in FIG. 1, i.e., the state where the projection 22 is placed at the distal end part of the linear groove 16 serving as the initial reference.

In this initial state, when the mouth piece 8 is further pulled with respect to the outer tube 4 from the initial state, the projection 22 enters the loop-like groove 19 and the inner tube 5 can thereby rotate freely. Therefore, in a case that a torsion force is stored in the inner tube 5, the stored torsion force is released. That is, the projection 22 moves along the loop-like groove 19, the inner tube 5 together with the needle body 12 takes one rotation to release the twist of the inner tube 5. As a result, since the inner tube will not take over one rotation, a failure operation caused by the twist will not occur.

On the other hand, after the treatment is finished, the outer tube 4 led out from the proximal end of the instrument, e.g., an endoscope and the like is pulled, and the tissue insertion portion 13 of the needle body 12 is removed from the tissue. The mouth piece 8 is pulled, and the needle body 12 is accommodated in the outer tube 4.

At last, the entire injection needle apparatus 1 for an endoscope is removed from, e.g., an endoscope or the like in this needle body accommodated state.

According to the injection needle apparatus of this embodiment, a direction of the needlepoint 14 of the needle body 12 can be rotated step by step at each given angle by the simple operation of pulling out and pushing in the inner tube 5. Therefore, as shown in FIG. 11B, the needlepoint 14 can be inserted into a living tissue in a state where the needle point 14 points downward with respect to the living body tissue. Consequently, even if it can approach the surface of the living body tissue only in a state an angle of the endoscope with respect to the living body tissue surface is very small, the needlepoint 14 can be inserted in the living body tissue without slipping.

Since the insertion can be made at such an angle, when making an insertion in a blood vessel, as shown in FIG. 11B, the insertion can be made in the blood vessel at an angle close to a horizontal state, and hence the needlepoint 14 can be surely arranged in the blood vessel without finely controlling a depth of insertion in a living body tissue. Further, since the needlepoint 14 can point downward, the opening 15 at the needle distal end faces up with respect to the tissue surface so that it takes a state shown in FIG. 12B in the blood vessel and hence the supplying property of, e.g., the liquid medicine and the like is not degraded.

According to this embodiment, the direction of the needlepoint can be adjusted step by step at each given angle. Therefore, a good insertion property and a good liquid supplying property with respect to a living body tissue in a body cavity can be obtained.

In this embodiment, the projection 22 is provided on the outer tube 4 and the spiral grooves 17 are provided on the inner tube 5. However, the members on which the projection 22 and the spiral grooves 17 are provided may be counterchanged. The spiral grooves 17 may be provided on the outer tube 4 and the projection 22 may be provided on the inner tube 5 to achieve the above-explained relationship. Further, in this embodiment, the spiral grooves 17 are formed in such a manner that the needlepoint 14 of the needle body 12 rotates when pulling the hollow needle body 12 into the outer tube 4. But, the rotation mechanism may be configured in such a manner that the needlepoint 14 rotates when projecting the needle body 12.

Next, an injection needle apparatus according to another embodiment of the present invention will now be explained with reference to FIGS. 7 to 10. In the injection needle apparatus according to this embodiment, like reference numerals denote members equal to those in the injection needle apparatus according to the foregoing embodiment.

Like the injection needle apparatus 1 for an endoscope according to the foregoing embodiment, an injection needle apparatus 1 according to this embodiment is configured to be divided into an inserting portion 2 and an operating portion 3. The inserting portion 2 has a flexible outer tube (an outer sheath) 4 and a flexible inner tube 5, and the inner tube 5 is inserted in the outer tube 4 to allow its forward and back movements. Both the outer tube 4 and the inner tube 5 have a relationship that they can relatively move in an axial direction of the inserting portion 2. Each of the outer tube 4 and the inner tube 5 is formed of a resin having elasticity, e.g., a fluoroplastic, polyethylene, polyamide, and the like.

Figure 7:
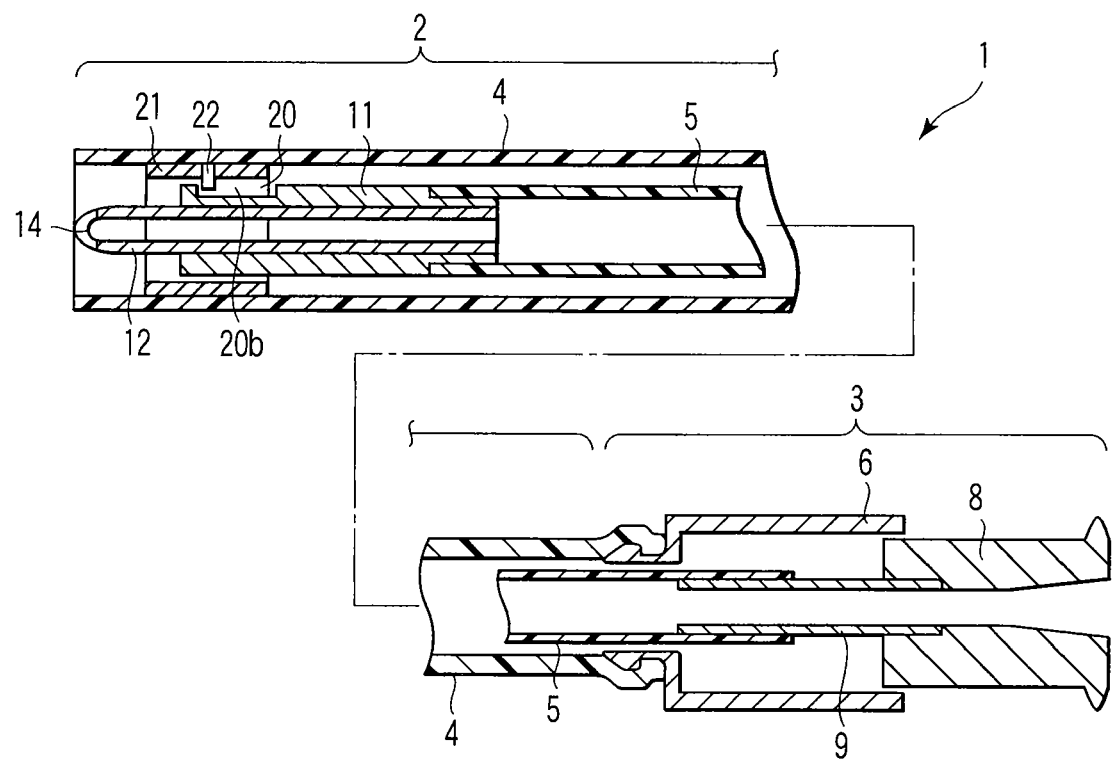
FIG. 7 is a vertical cross-sectional view of an injection needle apparatus for an endoscope, according to another embodiment of the present invention.

As shown in FIG. 7, the operating portion 3 includes an operating portion main body 6 and a mouth piece 8 serving as a slide operation member that can freely move in a back-and-forth direction with respect to this operating portion main body 6. A proximal end of the outer tube 4 is attached and fixed to the member of the operating portion main body 6 by fixing means, e.g., press fitting, an adhesive, and the like. The mouth piece 8 is fixedly connected with a proximal end part of the inner tube 5 through a hard pipe 9 by, e.g., press fitting, an adhesive, and the like. The mouth piece 8 communicates with the inner tube 5 via the hard pipe 9. A non-illustrated syringe for injecting a liquid medicine can be detachably attached to the mouth piece 8.

A cylindrical hard adapter 11 is fixed to a distal end of the inner tube 5 by fixing means, e.g., an adhesive, caulking, and the like. A hollow needle body 12 is fitted in this adapter 11. The adapter 11 and the hollow needle body 12 are fixed by fixing means, e.g., an adhesive, caulking, and the like, in a state where a distal end part of the needle body 12 projects from a distal end of the adapter 11 to be exposed. The adapter 11 and the needle body 12 are coaxially arranged. A distal end part for insertion of the needle body 12 projecting from the distal end of the adapter 11 is narrower than a diameter of the adapter 11, and the distal end part projecting from the distal end of the adapter 11 and exposing constitutes a tissue insertion portion 13 (see FIG. 8). The adapter 11 and the needle body 12 are coaxially arranged, and both these members constitute a distal end needle portion.

Figure 8:
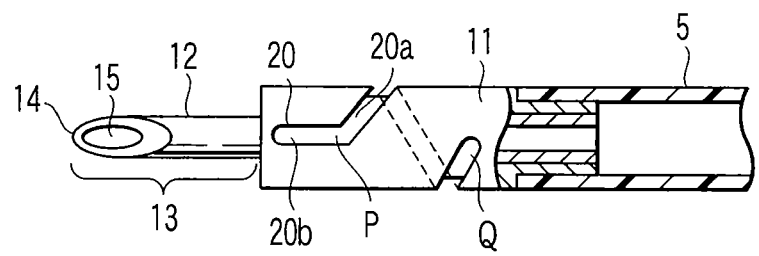
FIG. 8 is a plan view showing a distal end needle portion of the injection needle apparatus for an endoscope, according to the other embodiment of the present invention, a part of the needle portion being cut.

As shown in FIGS. 8 and 9, the adapter 11 projects from the distal end of the inner tube 5. The distal end part of the needle body 12 further projects from the distal end of the adapter 11. An endmost part of the needle body 12 is obliquely cut, and a needlepoint 14 having a sharp shape and a distal end opening 15 are thereby formed. As shown in FIGS. 1 and 2, the exposed part of the adapter 11 projecting from the distal end of the inner tube 5 is formed to have an external diameter substantially equal to an external diameter of the inner tube 5.

As shown in FIG. 8, the exposed outer peripheral part of the adapter 11 is formed to have an external diameter substantially equal to the external diameter of the inner tube 5. A groove 20 that engages with a later-explained projection 22 is formed in the exposed outer peripheral surface of the adapter 11. A proximal end side part of the groove 20 is formed into a single spiral groove 20a. The spiral groove 20a is formed as a groove that spirally circles at an angle of approximately 360°. A distal end side part of the groove 20 extends forward as a linear groove 20b parallel to a longitudinal axial direction of the inner tube 5.

As shown in FIG. 8, both terminal ends P and Q of the spiral groove 20a are placed at the same position in a circumferential direction of the hollow needle body 12, and the positions of the both terminal ends P and Q also correspond to a position of the distal end opening 15 of the needlepoint 14. A width of the groove 20 is approximately 0.5 mm and a depth thereof is approximately 0.3 mm.

Furthermore, as shown in FIG. 9, a pipe-like member 21 formed of a resin or a metal material is arranged on an inner surface of a distal end part of the outer tube 4 corresponding to the distal end needle portion 13, and the pipe-like member 21 is fixed to the outer tube 4 by an adhesive or press fitting. The cylindrical or semispherical projection 22 is formed on an inner surface of this pipe-like member 21 to project toward the inner side of the outer tube 4, and a distal end part of this projecting projection 22 is always set in and engaged with the above described groove 20. Dimensions of the projecting part of this projection 22 is set to approximately 0.4 mm in its diameter and set to approximately 0.2 mm in its height, and the dimensions are set to allow its movement without coming off the groove 20.

Next, an operation for using the injection needle apparatus 1 for an endoscope according to this embodiment will be explained. In a preparation stage for use, the mouth piece 8 is pulled with respect to the operating portion main body 6 of the operating portion 3 to retract and accommodate the needle body 12 in the outer tube 4, thereby providing a state shown in FIG. 7. In this accommodated state, the projection 22 is placed at a distal end side part of the linear groove 20b positioned on a distal end side of the groove 20.

Then, a syringe (not shown) filled with a liquid medicine is attached to the mouth piece 8 of the injection needle apparatus 1 for an endoscope, and the inserting portion 2 of the injection needle apparatus 1 for an endoscope is inserted into a channel of an endoscope or any other guide instrument to be led into a body cavity to make the distal end of the inserting portion 2 project in the body cavity.

Further, the mouth piece 8 is pushed toward the distal end side. Then, the projection 22 moves to a proximal end side in the linear groove 20b, and the hollow needle body 12 projects from the distal end of the outer tube 4 to set a state as shown in FIG. 9. And, at a time when the projection 22 reaches a distal end side terminal end P of the spiral groove 20a, the distal end of the adapter 11 slightly projects from the distal end of the outer tube 4. Therefore, the tissue insertion portion 13 of the needle body 12, i.e., the exposed part of the needle body 12 other than the part covered with the adapter 11 projects from the distal end of the outer tube 4.

In the state where the tissue insertion portion 13 of the needle body 12 projects in this manner, whether the needlepoint 14 points a tissue region side as an insertion target or not is confirmed by an instrument, e.g., the endoscope and the like. When the needlepoint 14 does not point the tissue region side as the insertion target, the mouth piece 8 is further pushed. As a result, the projection 22 enters a region of the spiral groove 20a and the projection 22 moves along the spiral groove 20a so that the needle body 12 is relatively rotated around a central axis of the inner tube 5 with respect to the outer tube 4 and the needle body 12 is relatively rotated with respect to the outer tube 4 in accordance with an amount of push-in rotation. At this time, since the outer tube 4 has a large frictional resistance with respect to the endoscope, the outer tube 4 does not rotate, but only the needle body 12 rotates to change a direction of the needlepoint 14 of the needle body 12. A range in which the direction of the needlepoint 14 of the needle body 12 changes is 360° that is a range of the spiral groove 20a, and the direction of the needlepoint 14 can be adjusted in this range by adjusting the amount of pushing of the mouth piece 8.

After the needlepoint 14 of the needle body 12 points the tissue region as the insertion target, the outer tube 4 led out from the proximal end of the endoscope is pushed into the endoscope so that the distal end part of the injection needle apparatus 1 is entirely projected from the endoscope to insert the tissue insertion portion of the needle body 12 in the tissue.

At this time, since the external diameter of the adapter 11 is larger than the external diameter of the needle body 12, this stepped end surface part functions as a stopper, and any other part of the needle body 12 than the tissue insertion portion 12a is not inserted in the tissue.

Then, an injecting operation of the syringe is performed to inject the liquid medicine and the like into the tissue via the inside of the mouth piece 8, the inside of the inner tube 5, and the inside of the needle body 12, thereby performing the predetermined injection.

After this treatment is performed, the outer tube 4 led out from the distal end of the endoscope is pulled with respect to the endoscope 4 to remove the tissue insertion portion 12a of the needle body 12 from the tissue. The mouth piece 8 is pulled with respect to the operating portion main body 6 to accommodate the tissue insertion portion 12a of the needle body 12 in the outer tube 4.

Finally, the entire injection needle apparatus 1 in this state is removed from the endoscope.

With the injection needle apparatus according to this embodiment, the direction of the needlepoint 14 of the needle body 12 can be continuously changed by varying a projecting amount of the needle body 12 from the outer tube 4 so that a state where the needlepoint 14 points downward with respect to a surface of a tissue region can be selected to make an insertion in the tissue part as shown in FIG. 11B. As a result, even if the endoscope can approach a tissue surface only with a very small angle of the endoscope with respect to the tissue surface, the needlepoint 14 can be surely inserted in the tissue without slipping.

Since the insertion can be made at such an inclined angle, even if the insertion is made in a blood vessel, the insertion can be made in the blood vessel at an angle close to a horizontal state. And, the needlepoint 14 can be inserted in the blood vessel to be located in the blood vessel without finely controlling an amount of the insertion in the tissue.

Moreover, since the needlepoint 14 of the needle body 12 can be made to point downward, the opening at the needle distal end faces upward with respect to the tissue surface so that it takes a state as shown in FIG. 12B in a blood vessel and does not prevent the liquid supply property for a liquid medicine and the like.

According to this embodiment, since a direction of the needlepoint of the needle body can be arbitrarily and surely adjusted in a body cavity, a good insertion property and a liquid supply property to a tissue in a body cavity can be obtained.

In this embodiment, the projection 22 is provided on the outer tube 4 side and the spiral groove 20a is provided on the inner tube 5 side. However, in contrast thereto, the spiral groove 20a may be provided on the outer tube 4 and the projection 22 may be provided on the inner tube 5 side. In this case, the linear groove 20b is continuous with the proximal end of the spiral groove 20a and linearly extends in the longitudinal direction of the inner tube.

Additionally, in this embodiment, the spiral groove 20a is provided in such a manner that the needlepoint 14 of the needle body 12 rotates when the hollow needle body 12 is pulled into the outer tube 4. But, it may be configured in such a manner that the needlepoint 14 rotates when the needle body 12 is projected out.

Further, the present invention is not restricted to the above mentioned embodiments, and it can be likewise applied to any other embodiments.

The invention claimed is:

1. An injection needle apparatus suitable for forming an injection in a tissue in a body cavity, the apparatus comprising:
   an elongated outer tubular member that is configured to be inserted into the body cavity and has a central axis in a longitudinal direction;
   an elongated flexible inner tubular member that is inserted into the outer tubular member, movable in the longitudinal central axis direction of the outer tubular member, rotatable about the longitudinal central axis of the outer tubular member, and has its respective central axis in a longitudinal direction;
   a needle body for insertion that is supported at a distal end part of the inner tubular member and has a distal end sharp part eccentrically arranged from the longitudinal central axis to a lateral side of the inner tubular member;
   an operating portion that is located on a proximal end side of the inner tubular member, configured to operate a proximal end part of the inner tubular member to move the inner tubular member in the longitudinal axis direction of the outer tubular member, and to project and retract the needle body from and into a distal end of the outer tubular member; and
   a needle body rotation operating device that is interposed between the distal end part of the inner tubular member and the distal end part of the outer tubular member, and configured to completely rotate the needle body around the central axis in the longitudinal axis direction of the inner tubular member through rotation angles corresponding to the number of times the inner tubular member is moved in the longitudinal axis direction, to change a rotational and not axial position of the distal end sharp part.

2. The injection needle apparatus according to claim 1, wherein the needle body rotation operating device includes:
   a plurality of needle direction regulating grooves that are provided on an outer periphery at the distal end part of the inner tubular member, arranged on a circumference around the central axis in the longitudinal direction of the inner tubular member to be apart from each other, linearly extend in the longitudinal central axis direction of the inner tubular member, and respectively determine a rotation position of the needle body around the central axis in the longitudinal direction of the inner tubular member;
   a communication groove that is provided on the outer periphery at the distal end part of the inner tubular member and connects the needle direction regulating grooves adjacent to each other; and
   a projection that is provided on the outer tubular member, fitted in the grooves, and moves from the needle direction regulating groove to the adjacent needle direction regulating groove via the communication groove by the movement of the inner tubular member in the longitudinal central axis direction, thereby rotating the insertion needle body around the central axis in the longitudinal direction of the inner tubular member.

3. The injection needle apparatus according to claim 1, wherein the needle body rotation operating device includes:
   a plurality of needle direction regulating grooves that are provided on an inner periphery at the distal end part of the outer tubular member, arranged on a circumference around the central axis in the longitudinal direction of the inner tubular member to be apart from each other, linearly extend in the longitudinal central axis direction of the outer tubular member, and respectively determine a rotation position of the needle body around the central axis in the longitudinal direction of the inner tubular member;
   a communication groove that is provided on the inner periphery at the distal end part of the outer tubular member and connects the needle direction regulating grooves adjacent to each other; and
   a projection that is provided on the inner tubular member, fitted in the grooves, and moves from the needle direction regulating groove to the adjacent needle direction regulating groove via the communication groove by the movement in the longitudinal central axis direction of the inner tubular member, thereby rotating the insertion needle body around the central axis in the longitudinal direction of the inner tubular member.

4. The injection needle apparatus according to claim 2, including a course switching guide portion that is provided at a junction of the needle direction regulating groove and communication groove, and performs a non-return function allowing a movement of the projection from the needle direction regulating groove to the communication groove only when pulling the inner tubular member into the operating portion side with respect to the outer tubular member by an operation of the operating portion.

5. The injection needle apparatus according to claim 3, including a course switching guide portion that is provided at a junction of the needle direction regulating groove and communication groove, and performs a non-return function allowing a movement of the projection from the needle direction regulating groove to the communication groove only when pulling the inner tubular member toward the operating portion side with respect to the outer tubular member by an operation of the operating portion.

6. The injection needle apparatus according to claim 4, wherein the course switching guide portion includes a projection or a step.

7. The injection needle apparatus according to claim 2, including a loop groove that is provided on the outer periphery at the distal end part of the inner tubular member, continuous with a proximal end of at least one of the needle direction regulating grooves, and circulates around the central axis in the longitudinal direction of the inner tubular member, the loop groove allowing a free rotation of the inner tube and releasing a distortion of the inner tubular member when the projection is introduced in the loop groove.

8. The injection needle apparatus according to claim 3, including a loop groove that is provided on the inner periphery at the distal end part of the outer tubular member, continuous with a proximal end of at least one of the needle direction regulating grooves, and circulates around the central axis in the longitudinal direction of the inner tubular member, the loop groove allowing a free rotation of the inner tube and releasing a distortion of the inner tubular member when the projection is introduced in the loop groove.

9. The injection needle apparatus according to claim 2, wherein the communication groove spirally circles around the central axis in the longitudinal direction of the inner tubular member.

10. The injection needle apparatus according to claim 3, wherein the communication groove spirally circles around the central axis in the longitudinal direction of the inner tubular member.

11. The injection needle apparatus according to claim 5, wherein the course switching guide portion includes a projection or a step.

12. The injection needle apparatus according to claim 4, including a loop groove that is provided on the outer periphery at the distal end part of the inner tubular member, continuous with a proximal end of at least one of the needle direction regulating grooves, and circulates around the central axis in the longitudinal direction of the inner tubular member, the loop groove allowing a free rotation of the inner tube and releasing a distortion of the inner tubular member when the projection is introduced in the loop groove.

13. The injection needle apparatus according to claim 6, including a loop groove that is provided on the outer periphery at the distal end part of the inner tubular member, continuous with a proximal end of at least one of the needle direction regulating grooves, and circulates around the central axis in the longitudinal direction of the inner tubular member, the loop groove allowing a free rotation of the inner tube and releasing a distortion of the inner tubular member when the projection is introduced in the loop groove.

14. The injection needle apparatus according to claim 5, including a loop groove that is provided on the inner periphery at the distal end part of the outer tubular member, continuous with a proximal end of at least one of the needle direction regulating grooves, and circulates around the central axis in the longitudinal direction of the inner tubular member, the loop groove allowing a free rotation of the inner tube and releasing a distortion of the inner tubular member when the projection is introduced in the loop groove.

15. The injection needle apparatus according to claim 11, including a loop groove that is provided on the inner periphery at the distal end part of the outer tubular member, continuous with a proximal end of at least one of the needle direction regulating grooves, and circulates around the central axis in the longitudinal direction of the inner tubular member, the loop groove allowing a free rotation of the inner tube and releasing a distortion of the inner tubular member when the projection is introduced in the loop groove.

16. The injection needle apparatus according to claim 4, wherein the communication groove spirally circles around the central axis in the longitudinal direction of the inner tubular member.

17. The injection needle apparatus according to claim 6, wherein the communication groove spirally circles around the central axis in the longitudinal direction of the inner tubular member.

18. The injection needle apparatus according to claim 7, wherein the communication groove spirally circles around the central axis in the longitudinal direction of the inner tubular member.

19. The injection needle apparatus according to claim 5, wherein the communication groove spirally circles around the central axis in the longitudinal direction of the inner tubular member.

20. The injection needle apparatus according to claim 11, wherein the communication groove spirally circles around the central axis in the longitudinal direction of the inner tubular member.

21. The injection needle apparatus according to claim 8, wherein the communication groove spirally circles around the central axis in the longitudinal direction of the inner tubular member.

* * * * *